US00PP27651P2

(12) United States Plant Patent
Horvath

(10) Patent No.: US PP27,651 P2
(45) Date of Patent: Feb. 7, 2017

(54) ***FESTUCA* PLANT NAMED 'COOL AS ICE'**

(50) Latin Name: ***Festuca* hybrid**
Varietal Denomination: Cool as Ice

(71) Applicant: Brent Horvath, Fontana, WI (US)

(72) Inventor: Brent Horvath, Fontana, WI (US)

( * ) Notice: Subject to any disclaimer, the term of this patent is extended or adjusted under 35 U.S.C. 154(b) by 0 days.

(21) Appl. No.: 14/756,731

(22) Filed: Oct. 6, 2015

(51) Int. Cl.
*A01H 5/12* (2006.01)

(52) U.S. Cl.
USPC ..... Plt./388

(58) Field of Classification Search
USPC ..... Plt./388
See application file for complete search history.

*Primary Examiner* — Annette Para

(57) ABSTRACT

A new, distinct *Festuca* plant as shown and described, characterized by gray green new growth that quickly matures to blue giving the plant better heat tolerance.

2 Drawing Sheets

Figure 1:
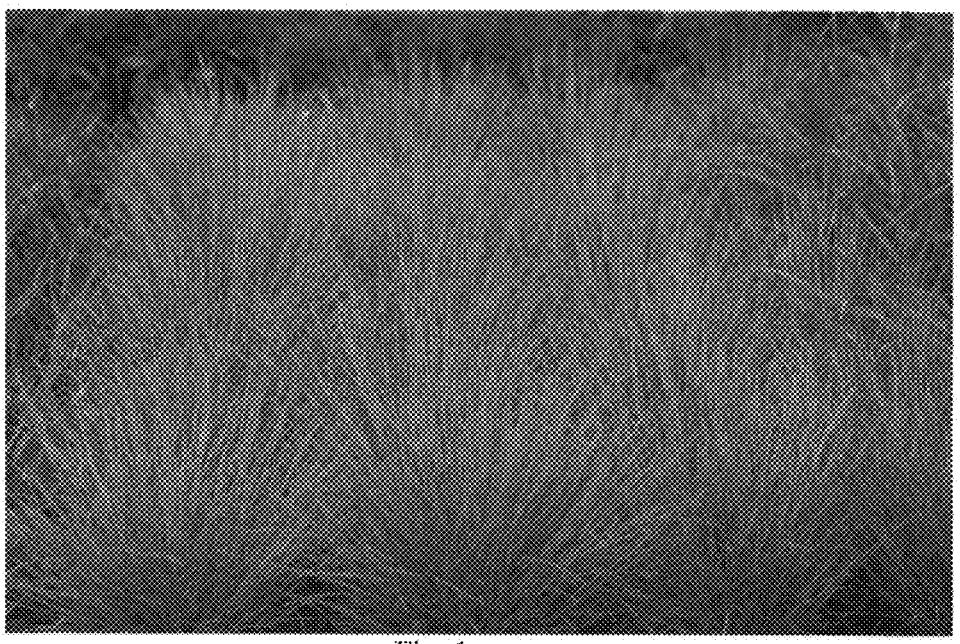

Latin name: *Festuca* hybrid.
Cultivar name: 'Cool as Ice'.

BACKGROUND OF THE INVENTION

The present invention relates to a new form of *Festuca* plant named 'Cool as Ice'. 'Cool as Ice' is a seedling of *Festuca*, not patented, characterized by gray green new growth that quickly matures to blue giving the plant better heat tolerance. The new plant was selected as a seedling by the inventor as part of an on going grass breeding program since 2009 at a wholesale perennial nursery in Hebron, Ill. in 2010. The selection of this plant was due to green new growth that quickly matures to blue giving the plant better heat tolerance. Asexual, vegetative division propagation has been the only means of reproduction. Propagation has taken place at a nursery in Hebron, Ill. since 2011. In 2011 we planted 60 plants in pots. To date these plants have remained uniform in height. The new *Festuca* has shown to be stable and identical in reproduction to the parent after making over 3000 vegetative divisions from 2011 to 2015.

SUMMARY OF THE INVENTION

In the following description, color references are made to The Royal Horticultural Society Colour Chart (2001). The following traits have been repeatedly observed and represent the characteristics of the new cultivar. The new *Festuca* has not been observed under all possible environmental conditions. These attributes in combination distinguish 'Cool as Ice' from all other selections of *Festuca* known to the Inventor. The new *Festuca* plant named 'Cool as Ice' has shown the characteristic of gray green new foliage that quickly turns to blue giving the plant better heat tolerance to be unique and stable.

Plants of the new *Festuca* can be compared to plants of *Festuca glauca* 'Elijah Blue', not patented. 1. The new *Festuca* has new growth in spring that emerges gray green and turns blue later in the season while plants of 'Elijahs Blue' new growth is blue. 2. The new *Festuca* has a foliage height of 30-35 cm compared to the height of 'Elijahs Blue' which has a foliage height of 15 cm.

Plants of the new *Festuca* can be compared to plants of Festuca 'Casca 11' U.S. Plant Pat. No. 23,307, patented. 1.

The new *Festuca* has an average foliage length of 33 cm compared to *Festuca* 'Casca 11' which has an average foliage length of 28.9 cm. 2. The new *Festuca* has thinner foliage colored 190 A with a width of 1 mm compared to *Festuca* 'Casca 11' which has mature colored foliage 189 B with an average foliage width of 1.8 mm.

Plants of the new *Festuca* can be compared to plants of *Festuca amethystina* 'Superba' not patented. 1. The new *Festuca* has a mature foliage height of 30-35 cm with color of 190 A compared to *Festuca amethystina* 'Superba' which has a mature foliage height of 30 cm color of 191 A. 2. The new *Festuca* has an inflorescence height of 45-50 cm compared to *Festuca amethystina* 'Superba' which has a mature inflorescence height of 60 cm.

DESCRIPTION OF PHOTOGRAPHS

The accompanying colored photographs illustrate the overall appearance and distinct characteristics of one year-old plants as grown in one gallon containers outdoors in Hebron, Ill., USA.

FIG. 1. Shows one gallon plants, blue foliage in May on an 8 month old plants.

Figure 2:
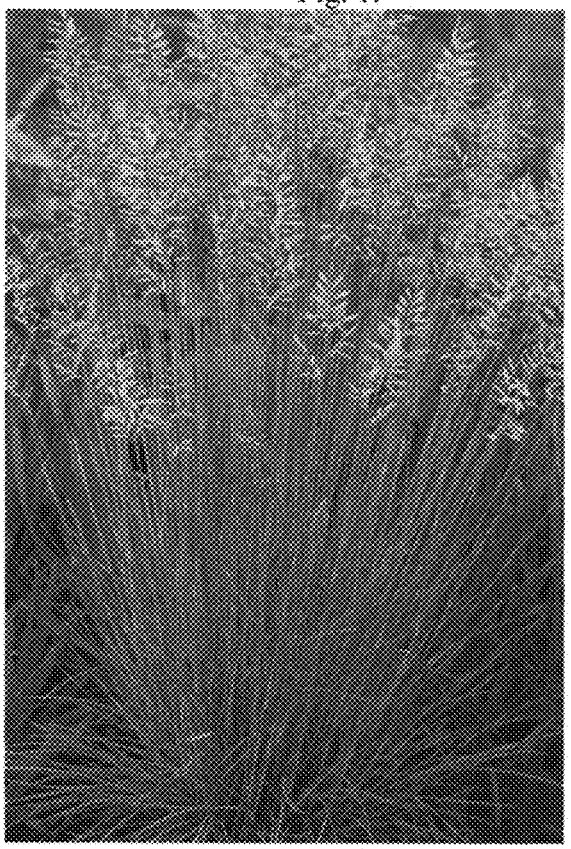

FIG. 2. Shows the overall plant habit and appearance in flower in a one gallon pot on a 9 month old plant in June.

Figure 3:
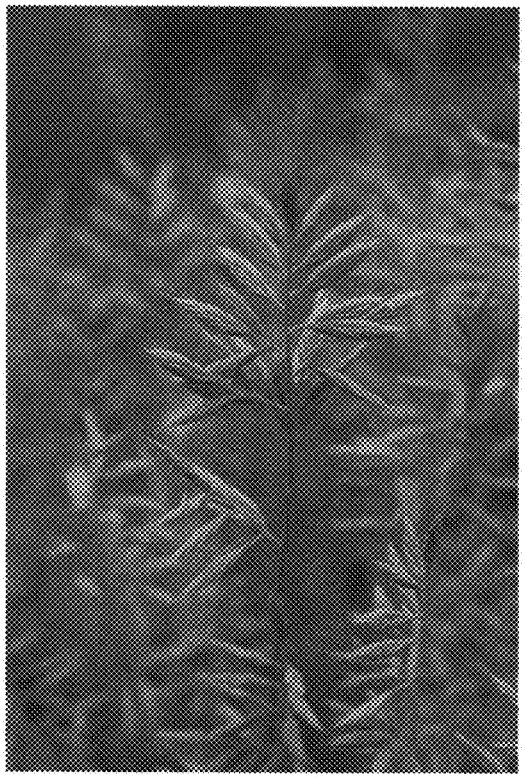

FIG. 3. Shows a close up of the emerging flower in June.

Figure 4:
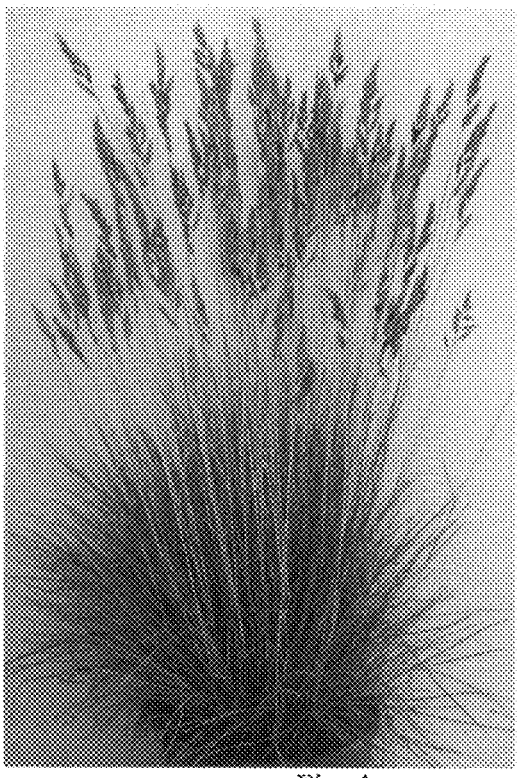

FIG. 4. Shows a mature plant with the flowers aging in July.

DETAILED BOTANICAL DESCRIPTION

In the following description, color references are made to The Royal Horticultural Society Colour Chart (2001). The plant herein described is a one year, one gallon specimen grown in full sun and irrigated in Hebron, Ill.

Botanical classification: *Festuca* cultivar 'Cool as Ice'.

Parentage: Unknown *Festuca* seedling.

Propagation: Vegetative division.

Plant description: Overall habit of the new *Festuca* is strongly clumping mounds with upright stems beginning in June and maturing to greyed yellow colored seed heads in September. Vigor is moderate.

*Plant height.*—45-50 cm.

*Plant width.*—50-60 cm.

*Flower stem diameter.*—1.5 mm.

Foliage:

*Plant type*.—Evergreen to semi-evergreen perennial grass, growing in culms 30-35 cm tall.

*Plant habit*.—Tufted, basal mounds.

*Shape*.—Filiform, blade.

*Petiole*.—None

*Apex*.—Acuminate.

*Aspect*.—Upright, then arching.

*Margins*.—Entire.

*Length*.—33 cm.

*Width*.—1 mm.

*Leaf number per shoot*.—4, over 200 shoots per one gallon container.

*Adaxial and abaxial leaf description*.—Surface — smooth, color — upon emerging is 137 B and upon maturing is 190 A.

Flower inflorescence:

*Inflorescence type*.—Terminal spike, loosely compacted.

*Inflorescence color*.—Upon opening the color is 163 D at the tips and 199 D at the base of the spikelets.

*Individual spikelets*.—Upon opening — size — 1-2 mm across, 7 mm long, color — 163 D at the tips and 199 D at the base. upon maturing — size — 1 mm across, 7 mm long, color — 161A.

*Overall inflorescence spike size*.—3 cm wide, 8 cm long.

*Flower number*.—Approximately 60-70 spikelets per mature spike measuring 3 cm wide, 8 cm long.

*Pedicel*.—Number — 80, color — 161 A, length up to spikelet 38 cm.

*Fertility*.—Fertile

*Blooming habit*.—Terminal spike on up to 45 cm stems.

*Bloom period and duration*.—June into September.

*Scent*.—No scent noticed.

*Bloom color*.—161 A.

*Roots*.—Fibrous.

*Fruit*.—Seed appears identical to the species Festuca glauca slightly larger.

*Hardiness*.—USDA Zones 4-8.

*Disease and pest resistance*.—Plants are not susceptible to any major pests or diseases.

*Culture*.—Tolerant to heat, humidity and drought.

Regarding, *Festuca* plant named 'Cool as Ice'

I claim:

1. A new, distinct *Festuca* plant as shown and described characterized by gray green new growth that quickly matures to blue giving the plant better heat tolerance.

* * * * *